US00PP09861P

United States Patent [19]

Moore et al.

[11] Patent Number: Plant 9,861

[45] Date of Patent: Apr. 15, 1997

[54] BLACKBERRY— KIOWA CULTIVAR

[75] Inventors: James N. Moore; John R. Clark, both of Fayetteville, Ark.

[73] Assignee: University of Arkansas, Fayetteville, Ark.

[21] Appl. No.: 553,962

[22] Filed: Nov. 6, 1995

[51] Int. Cl.[6] ..... A01H 5/00

[52] U.S. Cl. ..... Plt./46.1

[58] Field of Search ..... Plt./46.1

*Primary Examiner*—James R. Feyrer

[57] ABSTRACT

Description and specifications of a new and distinct blackberry variety which originated from seed produced by a hand pollinated cross of Arkansas Selection 791 (non-patented) and Arkansas Selection 1058 (non-patented) is provided. This new blackberry variety can be distinguished by its very large fruit size, erect canes, late ripening, long harvest period, and uniformly large fruits throughout the season.

2 Drawing Sheets

SUMMARY OF THE INVENTION

The new and distinct variety of blackberry originated from a hand pollinated cross of Arkansas Selection 791 (non-patented)×Arkansas Selection 1058 (non-patented) made in 1980 at the Arkansas Agricultural Experiment Station Fruit Substation at Clarksville, Ark. The parent plants used in this hybridization have not been named and released and are unavailable in commerce.

Plants and fruit of this new variety differ phenotypically from is parents. The new variety is eralier ripening and possesses better fruit firmness, greater vigor, and better fruit flavor than the parent Arkansas Selection 791, and is later ripening and more productive than the parent Arkansas Selection 1058. Initial fruit size of the new variety is similar to both parents, but it retains larger fruit size throughout the harvest season than either of the parent blackberries. Although blackberries (Rubus subg. Eubatus) are highly heterogeneous and outcrossing, and most clones contain genes from more than one species, the new variety and its progenitor lines phenotypically exhibit characters predominately of the erect eastern United States species, *Rubus allegheniensis* Porter (highbush blackberry) possibly introgressed with *R. argutus* Link. (tall blackberry).

The seeds resulting from this controlled hybridization were germinated in a greenhouse in the spring of 1981 and planted in a field on the Arkansas Agricultural Experiment Station in Clarksville, Ark. The seedlings fruited during the summer of 1983 and one, designated Ark. 1380, was selected for its very large fruit size, erect plant growth habit, and good fruit quality.

During 1983, the original plant selection was propagated asexually from root cuttings, at the above noted location, and a test row of 20 plants was established. Subsequently, larger test plantings have been established with asexualy multiplied plants at four additional locations in Arkansas and on state experiment stations in Missouri, Oklahoma, Kentucky and Texas.

The new variety has been asexually multiplied annually since 1983 by the use of root cuttings: it readily forms new plants from adventitious buds on root cuttings. During all asexual multiplication, the characteristics of the original plant have been maintained and no aberrant phenotypes have appeared.

Test plantings over a wide georgraphic area have shown this new variety to be adapted to differing soil and climatic conditions.

Plants of the new variety are moderately vigorous and prolific and row establishment following planting is rapid. Both primocanes and floricanes are moderately erect in growth habit but the new variety is not as rigidly erect as the Shawnee variety. The plants are moderately thorny, with size and density of thorns being similar to the Shawnee variety. Plants and fruit are moderately tolerant to anthracnose [*Elsinoe veneta* (Burkh.) Jenkins], and plants appear immune to orange rust [*Gymnoconia nitens* (Schwein.) F. Kern and H.W. Thurston.]. Budbreak in spring of the new variety averages 3 days earlier than Shawnee, but it blooms an average of 3 days later than Shawnee.

Fruit of the new variety begins ripening 3 days later than the Shawnee variety, and produces ripe fruit an average of 9 days longer than the Shawnee variety. Average ripening date is June 12 in central Arkansas. The harvest period is long, with ripening over a 6 week period, in contrast to most blackberry varieties that produce for 4 to 5 weeks. Fruit yields are comparable to the Choctaw variety but are less than yields of the Shawnee variety. Yields are consistent from year to year.

The fruit is blocky-oblong in shape, bright glossy black in color and very large in size (10–13 g). The fruit averages 30% larger than the Shawnee variety, and fruit size of the new variety does not decrease as the harvest season progresses as much as most blackberry varieties. The fruit is moderately firm at maturity, rating more firm than the Shawnee and Choctaw varieties, but less firm than the Navaho variety. Storage ability of fresh fruit of the new variety is superior to both the Shawnee and Choctaw varieties.

The fresh fruit rates good in flavor, being superior to the Shawnee variety, but less flavorful than the Choctaw and Navaho varieties. The flavor is sweet and mildly subacid, with a faint aroma reminiscent of wild blackberries. Flavor is sweeter and more aromatic than the Shawnee variety. The soluble solids concentration averages 10.3%, which is higher than most other blackberry varieties. Seed size averages 3.8 mg/seed, similar to the Shawnee variety, but is rated in test panel evaluations as being less "seedy" than Shawnee.

Fruit clusters are medium-large, cymose, and are mostly borne on the periphery of the plant canopy, providing easy access to harvest. Flower fertility is high and clusters are well filled.

The new variety has been named the KIOWA cultivar.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the botanical and pomological characteristics of the subject blackberry. Color data are presented in Royal Horticultural Society Colour Chart designations and are supplemented with readings from a Minolta Chroma Meter CR-200, version 3.0, which measures absolute chromaticity in tristimulus values Y, x, and y as determined by the Commission Internationale de l'Eclairage (CIE Yxy). Calibration was performed using a standard white plate supplied by the manufacturer.

Where dimensions, sizes, colors and other characteristics are given, it is to be understood that such characteristics are approximations of averages set forth as accurately as practicable.

The descriptions reported herein are from specimens grown at Clarksville, Ark. unless otherwise noted.

Plant

Size: Medium, erect.

Growth: Vigorous, prolific suckering from crowns, good suckering from roots.

Productivity: Medium and for duration of six weeks; consistent from year to year.

Cold Hardiness: Hardy to −23° C., similar to Shawnee.

Canes: Thorned, erect.

*Cane diameter.*—Base 1.5 cm, midpoint 1.0 cm, terminal 0.5 cm.

*Internode length.*—Base 4.5 cm, midpoint 3.6 cm, terminal 4.0 cm.

*Thorn density*/30 cm.—Base 77, midpoint 51, terminal 59.

*Floricane color.*—Base—Green (136A) Y=8.34, x=0.3748, y=0.3441; midpoint—Green (135B) Y=11.28, x=0.3724, y=0.3783; terminus—Green (136B) Y=12.66 x=0.3781, y=0.3869.

*Primocane color.*—Base—Green (141B) Y=16.46, x=0.3621, y=0.4223; midpoint—Green (141A) Y=13.04, x=0.3679, y=0.4223; terminus—Green (141B) Y=15.64, x=0.3734, y=0.4064.

*Date of primocane emergence.*—Julian 98.

*Date of budbreak.*—Julian 57.

Disease resistance: Moderate to anthracnose; immune to orange rust.

Foliage

Leaves: Large.

*Mature leaf diameter.*—6.7 cm.

*Length.*—9.7 cm.

*Color.*—Floricane base abaxial—Green (137C) Y=17.77, x=0.3478, y=0.4018; adaxial—Green (136A) Y=9.86, x=0.3436, y=0.4123; midpoint abaxial—Green (141B) Y=16.35, x=0.3428, y=0.3954; adaxial—Green (136A) Y=8.56, x=0.3323, y=0.3913; terminal abaxial—Green (141B) Y=15.93, x=0.3423, y=0.3925; Adaxial—Green (136A) Y=8.53, x–0.3326, y=0.3868. Primocane base abaxial—Green (141B) Y=17.77, x=0.3478, y=0.4018; adaxial—Green (136A) Y=9.86, x=0.3436, y=0.4123; midpoint abaxial—Green (143A) Y=18.87, x=0.3478, y=0.4000; adaxial—Green (132A) Y=9.71, x=0.3408, y=0.4100; terminal abaxial—Green (143A) Y=20.55, x=0.3532, y=0.4046; adaxial—Green (135B) Y=11.27, x=0.3450, y=0.4235.

Flowers

Date of bloom:

*First.*—Julian 104.

50%.—Julian 122.

*Last.*—Julian 150.

Blossom color: Red (49D) Y=61.26, x=0.3340, y=0.3251.

Reproductive organs:

*Stamens.*—Erect, numerous.

*Pistils.*—Numerous.

*Pollen.*—Normal and abundant.

Number flowers per cluster: 3 to 5.

Number of petals per flower: 5.

Peduncle length: 6.9 cm.

Fruit

Maturity: Late, 3 days after Shawnee. Average ripe date is June 12. Average period of ripening is June 12 to July 23.

Size: Very large, average 10.0 g, uniform.

*Diameter.*—Primary fruit at equator 2.33 cm, base pole 2.08 cm, terminal pole 1.40 cm; secondary fruit equator 2.07 cm., base pole 1.70 cm, terminal pole 1.18 cm.

Shape: Blocky-oblong, uniform.

Color: Glossy black; Black (202A) Y=3.43, x=0.3138, y=0.3129.

Drupelet size: Medium, 6.0 mm.

Seed size: Medium, 3.8 mg.

Soluble solids: 10.3%.

pH: 2.85.

Acidity: 1.90 g tartaric acid/100ml.

Anthocyanin (ABS, units/g): 139±20.

Processed quality: Good, similar to Choctaw, superior to Shawnee.

Uses: Fresh and processed, jellies, jams, juice, wine.

The Variety

The most distinctive features of the variety are its very large fruit size, late ripening, erect canes, long fruiting season, and ability to maintain large fruit size throughout the season.

We claim:

1. A new and distinct variety of blackberry plant, substantially as illustrated and described, characterized by its very large fruit size, erect canes, late ripening, long harvest period, and uniformly large fruits throughout the season.

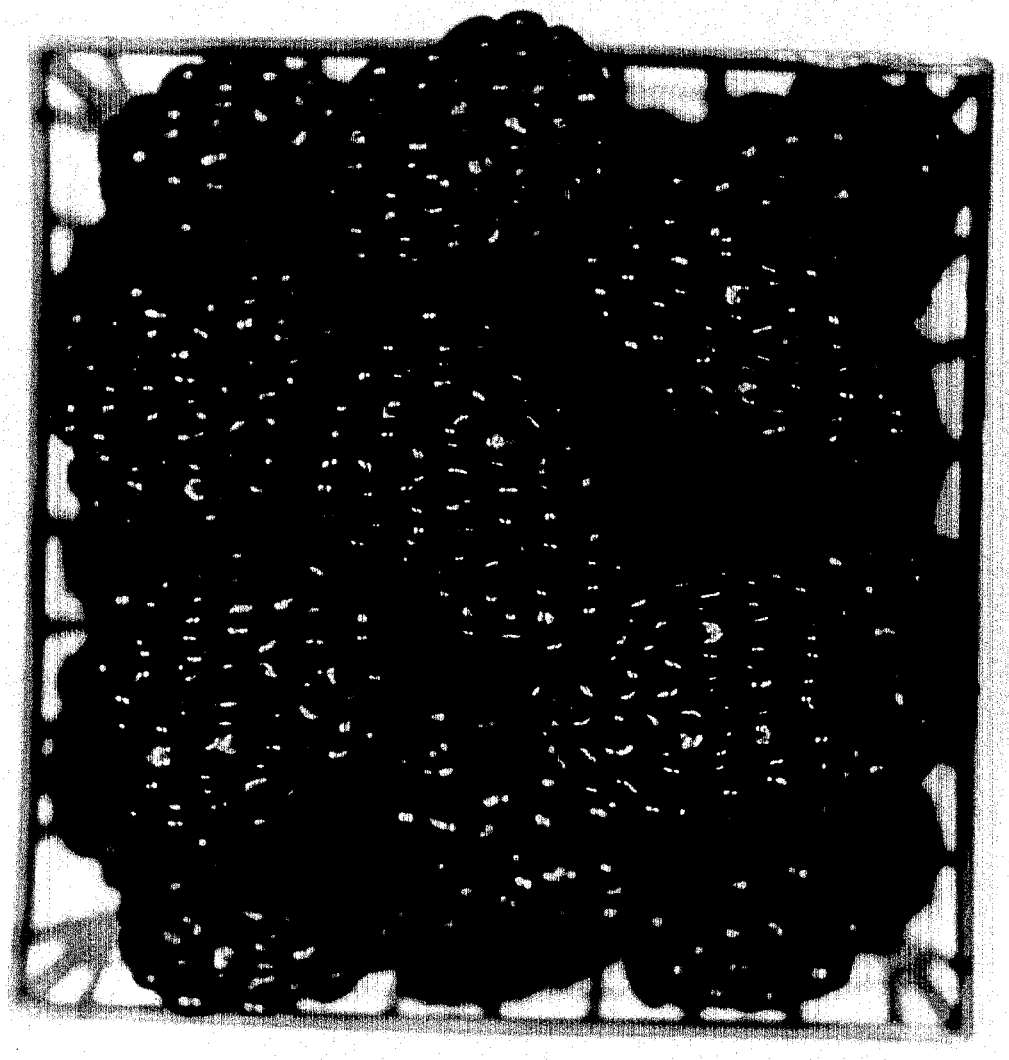

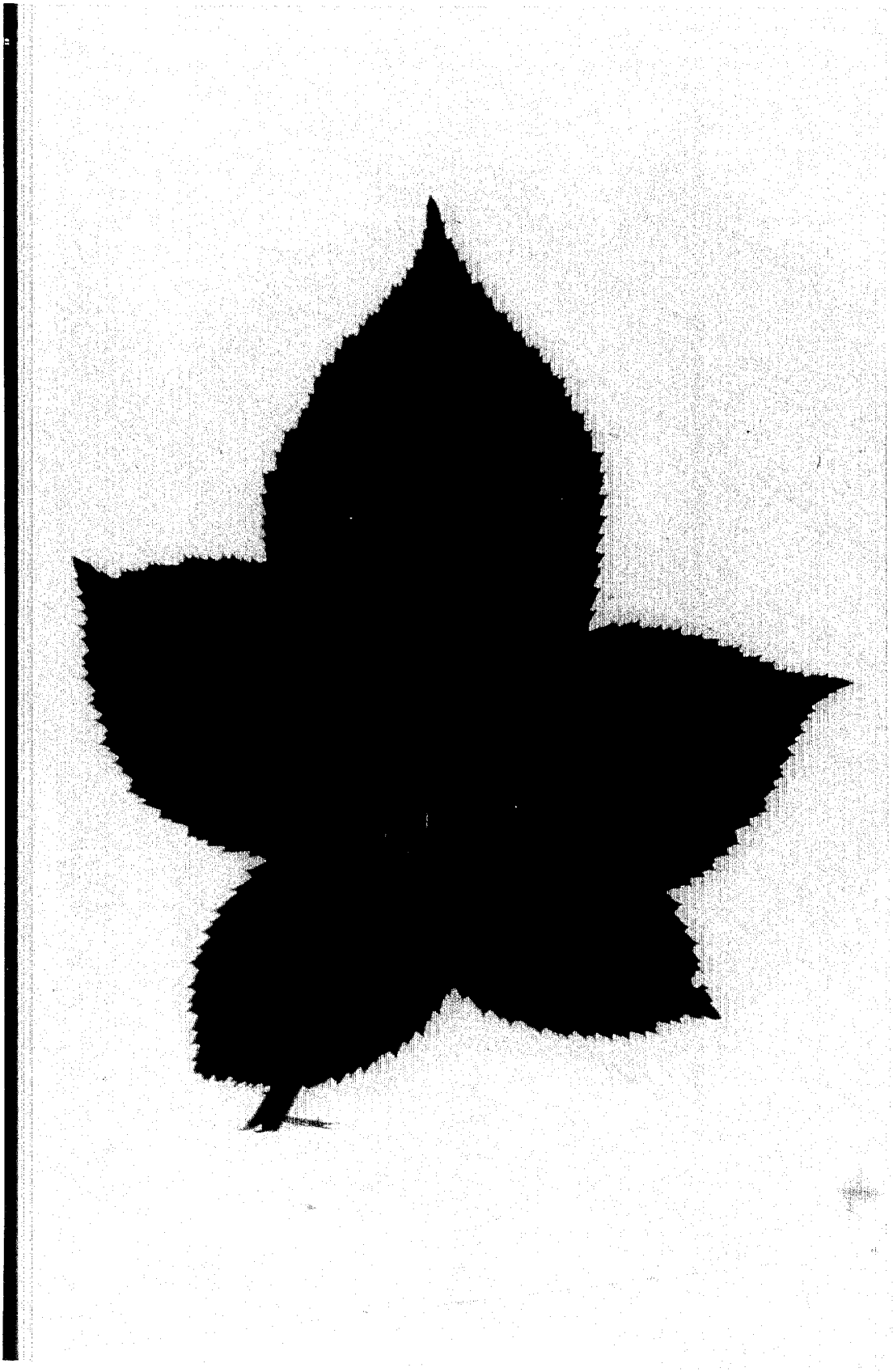

* * * * *